United States Patent [19]

Mead

[11] Patent Number: 4,848,916
[45] Date of Patent: Jul. 18, 1989

[54] BULK SODIUM BICARBONATE DIALYSIS SOLUTION MIXING APPARATUS

[76] Inventor: Brian Mead, 1059 W. LaJolla Dr., Tempe, Ariz. 85282

[21] Appl. No.: 147,890

[22] Filed: Jan. 25, 1988

[51] Int. Cl.⁴ .......................... B01F 5/12; B01F 15/02
[52] U.S. Cl. .................................... 366/137; 366/192; 366/262
[58] Field of Search ................ 366/96, 101, 107, 131, 366/132, 134, 136, 137, 138, 165, 192, 167, 173, 341, 262, 349; 137/577, 578, 590

[56] References Cited

U.S. PATENT DOCUMENTS

| | | | |
|---|---|---|---|
| 3,661,364 | 5/1972 | Lage | 366/136 |
| 3,871,272 | 3/1975 | Melandri | 366/137 X |
| 3,893,659 | 7/1975 | Krish | 366/137 |
| 4,084,796 | 4/1978 | Krehbiel | 366/137 |
| 4,472,064 | 9/1984 | Goins | 366/134 |
| 4,621,928 | 11/1986 | Schreiber | 366/165 |

Primary Examiner—Timothy F. Simone
Attorney, Agent, or Firm—Harry M. Weiss

[57] ABSTRACT

The present invention relates to an apparatus for mixing sodium bicarbonate solutions for kidney dialysis in quantities to sufficient to supply dialysate for multiple kidney dialysis patients. The inventive apparatus consists, generally, of a fluid container operably connected to a fluid recirculation pump for recirculating fluid in the fluid container. Attached to the fluid container are an evacuation tube, an overflow tube and an input tube.

The apparatus is operated by introducing medical grade water into the fluid container, recirculating the water, adding a premeasured quantity of bulk sodium bicarbonate solution and recirculating the mixture until the sodium bicarbonate solution is solubilized.

14 Claims, 2 Drawing Sheets

BULK SODIUM BICARBONATE DIALYSIS SOLUTION MIXING APPARATUS

BACKGROUND OF THE INVENTION

The present invention relates generally to a mixing apparatus for mixing particulate solids into solution, and in particular for mixing bulk solutions of sodium bicarbonate for kidney dialysis. More particularly, the present invention relates to an apparatus for mixing purified sodium bicarbonate solutions for kidney dialysis in quantities to sufficient to supply dialysate for multiple kidney dialysis patients.

Heretofore, dialysis technicians were required to mix separate quantities of sodium bicarbonate solution for each dialysis patient. Dialysis technicians usually mixed premeasured sodium bicarbonate concentrate with medical purified water. This procedure has been found to be both labor and time intensive as well as uneconomical. Efforts have been made to provide devices capable of mixing bulk sodium bicarbonate dialysis solutions to serve the needs of multiple patients. Exemplary of these devices is the RS-2500 Mixing System for Sodium Bicarbonate Hemodialysis Concentrate sold by Renal Systems, a division of Minntech Corporation of Minneapolis, Minn. Renal System's RS-2500 consists of a fifty gallon mixing drum, a free standing mixing and dispensing pump consisting of a pump attached to jet mixing tubing and dispensing tubing, and a separate pump disinfection container having a dispensing hose and nozzle assembly attached thereto. In operation the dialysis technician fills the mixing drum with purified water, adds pre-measured dry sodium bicarbonate dialysis concentrate to the mixing drum; inserts the mixing and dispensing pump into the mixing drum and operates the pump until the concentrate is fully solubilized into solution. Dispensing is accomplished by operating the mixing and dispensing pump to draw the sodium bicarbonate solution out of the mixing drum for dispensing into storage tanks or individual patient containers. While Renal System's RS-2500 provides a means for mixing bulk sodium bicarbonate solutions from concentrate, it is an open system which exposes the solution to the ambient atmosphere during mixing, thereby increasing the risks of contamination. Moreover, the apparatus remains awkward and cumbersome to use.

In contradistinction to conventional bulk sodium bicarbonate dialysis solution mixing devices, the present invention is a closed circuit and consists of a bulk mixing and storage container, a recirculating pump connected thereto by inflow and outflow tubing having a series of valves for controlling flow direction and dispensing. Dispensing is controlled by a dispensing valve located at a bottom outlet port of the container. At no time during the mixing is the solution exposed to the ambient atmosphere, thereby limiting and minimizing contamination risks.

It has been found, therefore, that a need has existed for a sodium bicarbonate dialysis solution mixing apparatus which operates in a closed circuit and consists of a mixing and storage container operably coupled to a recirculation pump through a series of conducting inflow and outflow tubing wherein the direction of the flow is controlled by a series of valves.

SUMMARY OF THE INVENTION

Accordingly, it is a broad object of the present invention to provide an apparatus for bulk mixing of a sodium bicarbonate dialysis solution.

It is another object of the present invention to provide a sodium bicarbonate dialysis solution mixing apparatus which operates in a closed circuit.

It is a more particular object of the present invention to provide a sodium bicarbonate dialysis mixing apparatus having a mixing and storage tank operatively coupled to a water source and a recirculating pump which recirculates water introduced into the mixing and storage tank, thereby solubilizing pre-measured sodium bicarbonate dialysis concentrate.

It is yet another object of the present invention to provide a sodium bicarbonate dialysis mixing apparatus having a plurality of control valves for controlling the inflow of water introduced into the mixing and storage tank, controlling the direction of flow within the apparatus and controlling dispensing of sodium bicarbonate dialysis solution from the apparatus.

It is still another object of the present invention to provide a sodium bicarbonate dialysis mixing apparatus having a diffusion baffle disposed adjacent to a dispensing outlet to prevent air infusion into the pump during mixing.

These and other objects, features and advantages of the sodium bicarbonate mixing apparatus will become more apparent from the following more detailed description of the preferred embodiment of the present invention with reference to the accompanying drawings, in which like features are identified by like reference numerals.

DETAILED DESCRIPTION OF THE PREFERRED EMBODIMENT

Figure 1:
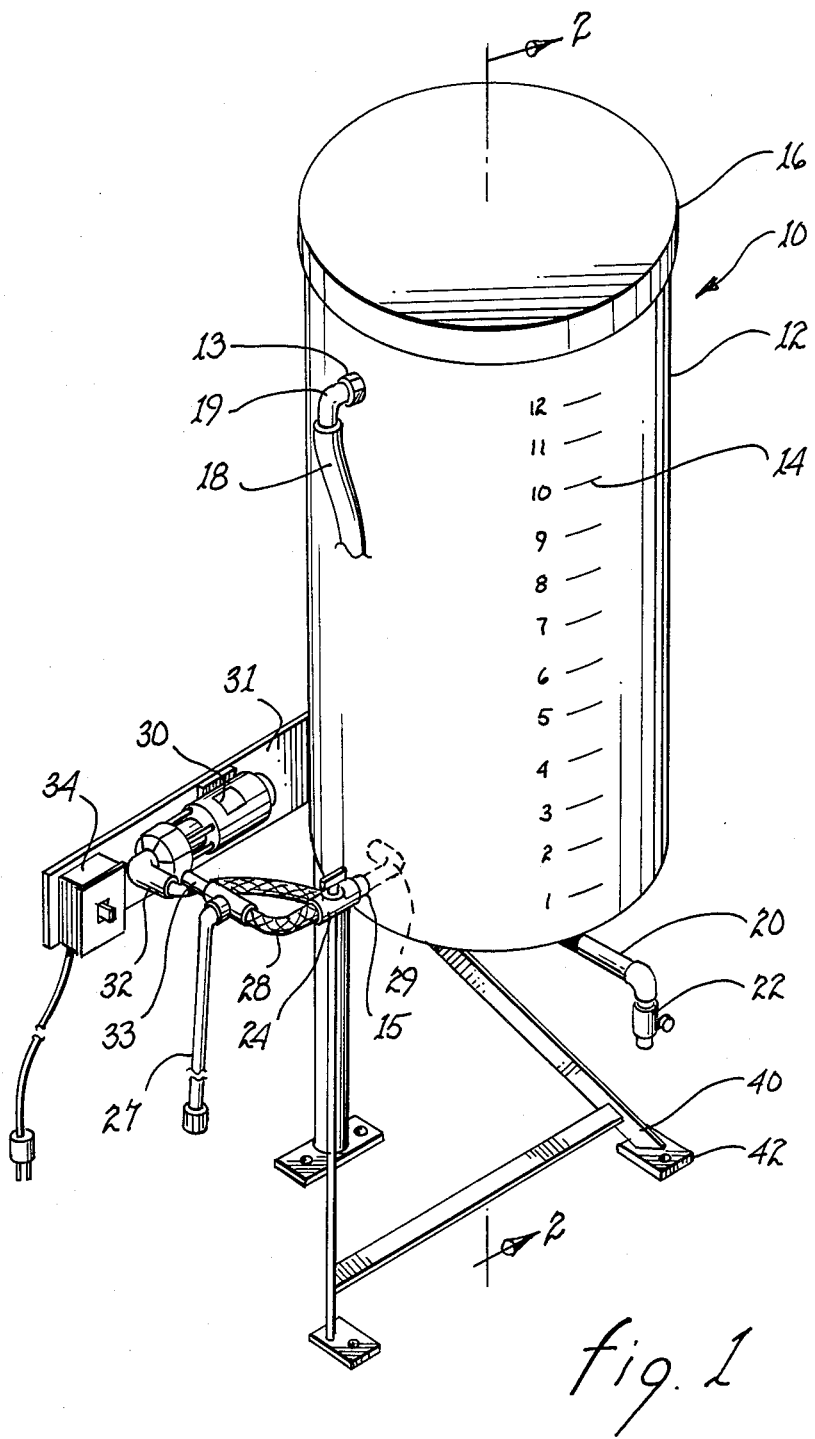
FIG. 1 is a perspective showing the bulk sodium bicarbonate dialysis solution mixing apparatus according to the present invention.
Figure 2:
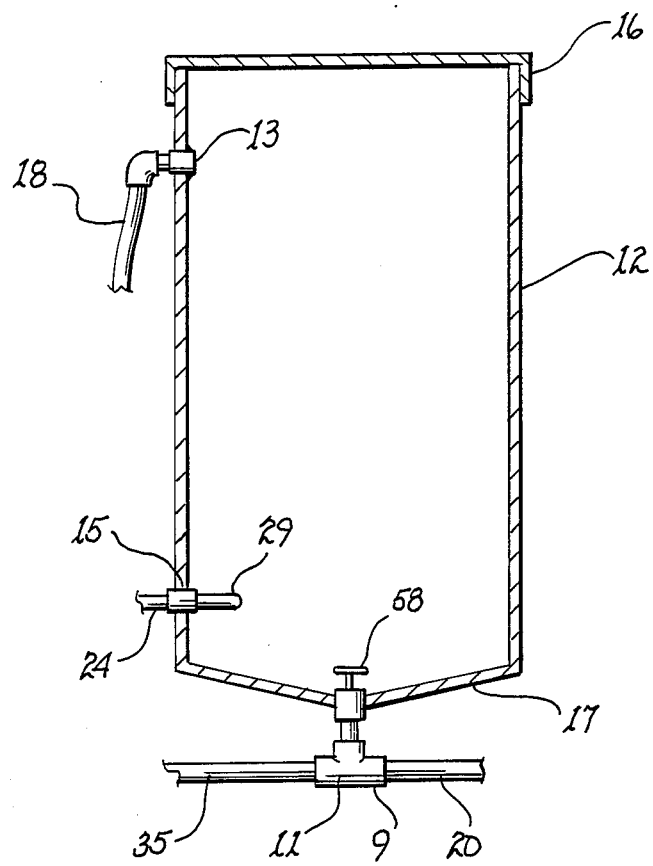
FIG. 2 is a partial cross-sectional view taken along line 2—2 of FIG. 1.
Figure 3:
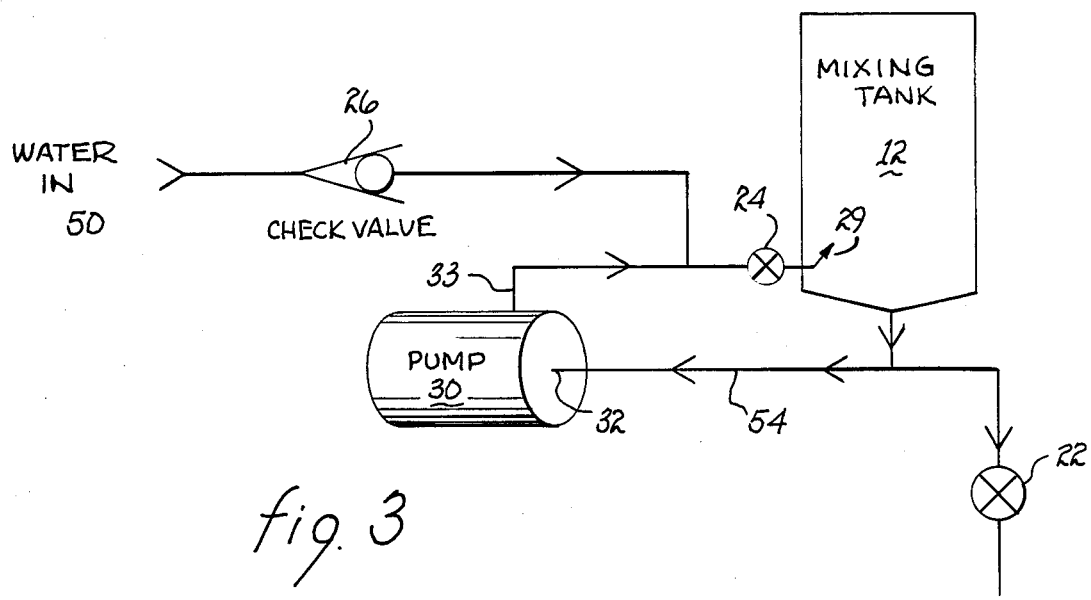
FIG. 3 is a schematic diagram illustrating the operative flow of the bulk sodium bicarbonate dialysis solution mixing apparatus according to the present invention.

With reference to the accompanying Figures, and with particular reference to FIG. 1, there is shown a bulk sodium bicarbonate dialysis solution mixing apparatus 10 according to the present invention. Apparatus 10 principally comprises a mixing and storage tank 12 having graduated measurements 14 in a suitable scale, such as number of pre-measured sodium bicarbonate packages, and a lid 16 which removably engages an upper lip portion of the mixing and storage tank 12. Mixing and storage tank 12 has a conical shaped bottom portion 17 thereof which terminates in a dispensing aperture 11 passing therethrough. A baffle 58 is disposed in close proximity and superior to dispensing aperture 11 to prevent sodium bicarbonate from obstructing dispensing aperture 11 and to prevent air infusion during recirculation. Along a lower side surface of mixing and dispensing tank 12 is disposed an inlet aperture 15 which permits a flow of liquid into an interior mixing chamber defined by mixing and storage tank 12. An overflow aperture 13 is provided at an upper side surface of mixing and dispensing tank 12 and connected to overflow tubing 18 by fitting 19 to permit overflow solution drainage and prevent spillage.

A recirculating pump 30 is coupled in fluid flow communication with mixing and storage tank 12 and provides the motivating force for the recirculation of fluid within mixing and storage tank 12. Recirculating pump 30 is preferably a 115 volt, 1.4 Amp, 60 Hz AC electrically grounded pump and is cycled on and off by switch 34 electrically coupled therewith. Switch 324 is preferably a timer actuated switch for the users convenience. Recirculating pump 30 has an inflow port 32 which draws fluid into the pump 30, and a corresponding outflow port 33 which ejects fluid under pressure from pump 30.

Outflow port 33 is connected in fluid flow communication with an inflow aperture 15 of mixing and dispensing tank 12. A tee-fitting 26 is coupled to outflow port 33, to a backflush valve 24 at one opening thereof, and to water tubing 27 at another opening thereof. Recirculation tubing 28, 35 is provided in two component pieces. First recirculation tubing 28 is used to connect one opening of tee-fitting 26 to backflush valve 24. Backflush valve 24 is, in turn, interdisposed between the tee-fitting 26 and inlet aperture 15 of the mixing and dispensing tank 12 and directs the output flow of solution from pump 30 to either inlet aperture 15 or water hose 27. Second recirculation tubing 35 is connected at one end thereof, to the inflow port 32 of the recirculation pump 30, and is connected, at a second end thereof, to a tee-fitting 9, coupled in fluid flow communication with dispensing aperture 11. Tubing 28 preferably consists of flexible tubing to isolate any vibrations in the mixing and dispensing tank 12 from the recirculating pump 30, although those skilled in the art will recognize the utility of rigid tubing as well.

An elbow fitting 29 is coupled to an interior exposure of inlet aperture 15 within the mixing and dispensing tank 12. Elbow fitting 29 conducts the recirculating water flow from the backflush valve 24 into the mixing and storage tank 12. Optimum recirculation of the solution is achieved by providing a 90° elbow fitting 29 angled downwardly from the horizontal within the mixing and dispensing tank 12 to impart an eddy flow therein.

Mixing and storage tank 12 is mounted upon and supported by an elevating support stand 40 which is securely attached to mixing and storage tank 12 along a side surface and bottom surface thereof. It has been found preferable to attach a pump support arm 31 to elevating support stand 40 so that pump 30 and switch 34 are positioned in close proximity to the inlet aperture 15 and the outlet aperture 11 of the mixing and storage tank 12. It is desirable to configure elevating support stand 40 as a tripod, each of the three legs terminating in plates 42 which permit bolting or other means for attaching the elevating support stand 20 to a base or flooring. In this manner, the elevating support stand 20 provides a sound foundation upon which to operate the mixing and dispensing apparatus 10 of the present invention.

Mixed solution is withdrawn from the mixing and storage tank 12 by actuating a valve 22 and evacuating the mixed solution through dispensing tubing 20. Dispensing tubing 20 is coupled by tee-fitting 9 to outlet aperture 11 of the mixing and dispensing tank 12 at one end thereof, and to valve 22 at a terminal end thereof.

In operation, mixing and dispensing tank 12 is filled to a desired pre-determined level according to scale 14 on a side thereof, using medical quality purified water. Recirculating pump 30 is activated and allowed to run for a short period of time to develop uniform eddies in the recirculating water. It has been found that approximately 5 minutes is generally sufficient preliminary recirculation. After the lapse of a sufficient period of time, pre-measured commercially available sodium bicarbonate concentrate for kidney dialysis is added into the recirculating water. The recirculating pump 30 is run for a sufficient time period to permit complete solubilization of the sodium bicarbonate concentrate, and then shut off. The user may then evacuate desired quantities of mixed sodium bicarbonate solution through dispensing tubing 20. If introduction of the sodium bicarbonate causes an obstruction of the recirculating pump 30, the pump may be cleared by applying a positive water pressure at the purified water source and activating the backflush valve 24.

It has been found preferable to employ plastic materials for mixing and dispensing tank 12, all tubing, valves and fittings. The advantage of the plastic materials lies in each of cleaning with bleach or soap and water.

Thus, it is apparent that there has been provided, in accordance with the present invention and the preferred embodiments thereof, a bulk sodium bicarbonate dialysis solution mixing apparatus which meets and achieves the objects and advantages set forth herein.

The invention has been particularly described and illustrated with reference to certain embodiments thereof, but it is not intended that the invention be strictly limited to these embodiments. Those having ordinary skill in the art will recognize that variations and modifications differing from these embodiments, but falling within the spirit and scope of the invention, are possible. Other materials or configurations, for example, are contemplated by the present invention. All such variations and modifications as fall within the appended claims are therefore considered within the scope of the invention.

I claim:

1. An apparatus for mixing and dispensing a liquid solution therefrom, comprising:

a container having an open top portion for introducing materials to be mixed and an open lower portion for dispensing resultant mixed solution therefrom, said containers further comprising an outlet aperture in said open lower portion, an inlet aperture in a side portion of said container and in close proximity to said open lower portion of said container and an overflow aperture in a side portion of said container and in close proximity to said open top portion of said container;

a fluid recirculating pump electrically coupled to a power source, said recirculating pump having an input port and output port thereof;

a dispensing tube in fluid flow communication with said outlet aperture of said container an din fluid flow communication therewith; said dispensing tube coupled to and terminating with a dispensing valve;

overflow tubing coupled to said overflow aperture of said container and in fluid flow communication therewith;

recirculating tubing comprising a first recirculation tube coupled, in fluid flow communication at one end thereof, to said outlet aperture of said container and to said dispensing tubing, said first recirculation tube being further connected, at another end thereof, to said input port of said fluid recirculating pump and in fluid flow communication therebetween; said recirculation tubing further comprising a second recirculation tube connected, at one end thereof, to said inlet aperture passing through a side portion of said container and, at another end thereof, connected to said output port of said recirculating pump; and support stand means for elevating and supporting said container and said recirculating pump.

2. The mixing and dispensing apparatus according to claim 1, further comprising a backflush valve connected, at one end thereof, to said inlet aperture of said container, and connected, at another end thereof, to said second recirculation tube; said second recirculation tube being interdisposed between a teefitting coupled to said output port of said recirculating pump and said backflush valve, and further connected to a water source.

3. The mixing and dispensing apparatus according to claim 1, wherein said bottom portion of said container further comprises a funnel-shape terminating with said outlet aperture.

4. The mixing and dispensing apparatus according to claim 3, wherein said funnel-shaped bottom portion further comprises baffle means, disposed in close proximity and immediately superior to said outlet aperture, for preventing an outflow of a solid mixing material through said outlet aperture during mixing.

5. The mixing and dispensing apparatus according to claim 3, wherein said input aperture of said container further comprises an elbow fitting coupled to said inlet aperture and disposed within said container, said elbow fitting being positioned to direct a flow of fluid into said container and impart an eddy flow therein.

6. The mixing and dispensing apparatus according to claim 1, wherein said support stand further comprises a tripod configuration having an elongate leg to which said container is attached, a pair of angled legs depending from said elongate leg and a container support arm perpendicularly extending from said elongate leg to which said bottom portion of said container is attached.

7. The mixing and dispensing apparatus according to claim 6, wherein said support stand further comprises a pump support member to which said recirculating pump is attached.

8. The mixing and dispensing apparatus according to claim 7, wherein said elongate leg and said pair of angled legs further comprise a planar footing having at least one of a plurality of apertures passing therethrough for attaching said support stand to another surface.

9. An apparatus for mixing and dispensing bulk sodium bicarbonate solution for kidney dialysis, comprising:

a tank defining an inner mixing chamber having a top portion, a lower frusto-conical shaped portion and side portions thereof, said tank further comprising a plurality of apertures passing therethrough, said plurality of apertures comprising at least one fluid outlet aperture centrally disposed in said lower portion, at least one fluid inlet aperture disposed in at least one side portion of said container and in close proximity to said lower portion of said container and at least one overflow aperture in at least one side portion of said container and in close proximity to said top portion of said container;

a fluid recirculating pump electrically coupled to a power source, said recirculating pump having an input port and output port thereof;

a dispensing tube connected to said outlet aperture of said container and in fluid flow communication therewith; said dispensing tube coupled to and terminating with a dispensing valve;

overflow tubing coupled to said overflow aperture of said container and in fluid flow communication therewith;

recirculating tubing comprising a first recirculation tube connected, at one end thereof, to said outlet aperture of said container and to said dispensing tubing, said first recirculation tube being further connected, at another end thereof, to said input port of said fluid recirculating pump and in fluid flow communication therebetween; said recirculation tubing further comprising a second recirculation tube connected, at one end thereof, to said inlet aperture passing through a side portion of said container and connected, at another end thereof, to said output port of said recirculating pump backflush valve interdisposed between said inlet aperture of said container and a tee-fitting, said tee-fitting being interdisposed between said outflow port of said recirculating pump and said backflush valve and further connected to a water source; and support stand means for elevating and supporting said container and said recirculating pump.

10. The mixing and dispensing apparatus according to claim 9, wherein said funnel-shaped bottom portion further comprises baffle means, disposed in close proximity and immediately superior to said outlet aperture, for preventing an outflow of a solid mixing material through said outlet aperture during mixing.

11. The mixing and dispensing apparatus according to claim 9, wherein said input aperture of said container further comprises an elbow fitting coupled to said inlet aperture and disposed within said container, said elbow fitting being positioned to impart an eddy flow of fluid in said container.

12. The mixing and dispensing apparatus according to claim 9, wherein said support stand further comprises a tripod configuration having an elongated leg to which said container is attached, a pair of angled legs depending from said elongate leg and a container support arm perpendicularly extending from said elongate leg to which said bottom portion of said container is attached.

13. The mixing and dispensing apparatus according to claim 12, wherein said support stand further comprises a pump support member to which said recirculating pump is attached.

14. The mixing and dispensing apparatus according to claim 13, wherein said elongate leg and said pair of angled legs further comprise a planar footing having at least one of a plurality of apertures passing therethrough for attaching said support stand to another surface.

* * * * *